Sept. 22, 1959 E. S. BURDICK Plant Pat. 1,868
MACADAMIA TREE
Filed Nov. 7, 1957 2 Sheets-Sheet 1
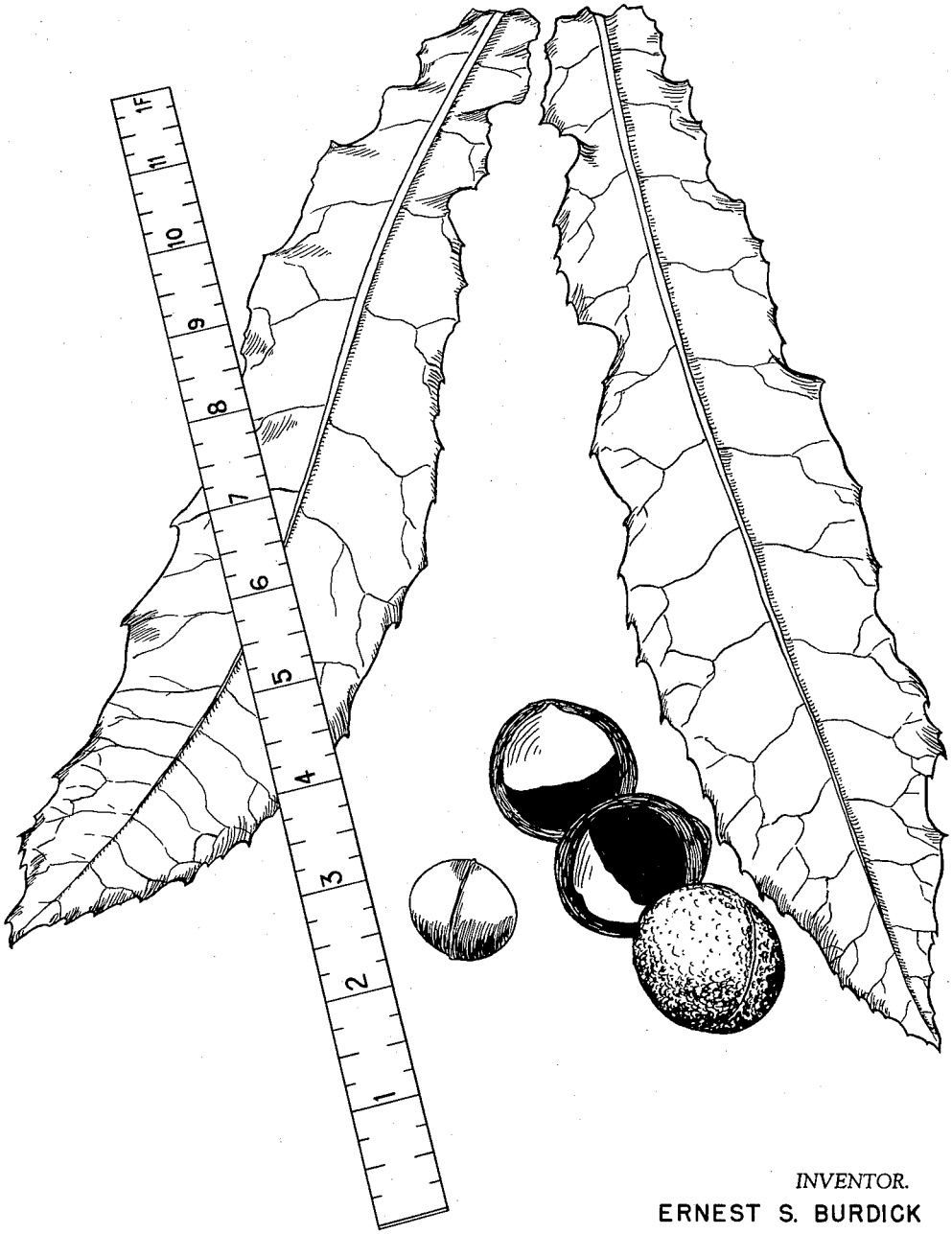
INVENTOR.
ERNEST S. BURDICK
BY
Knox & Knox MACADAMIA TREE
Filed Nov. 7, 1957 2 Sheets-Sheet 2
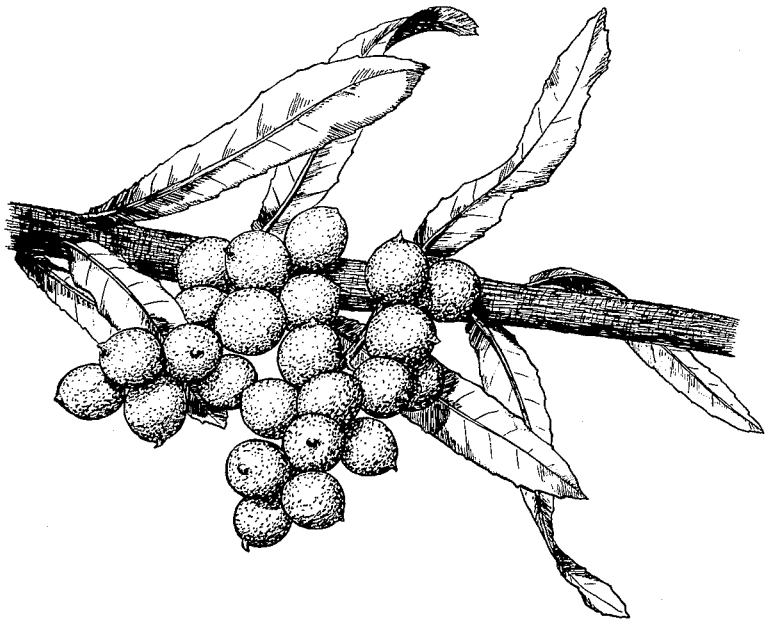
*INVENTOR.*
ERNEST S. BURDICK
*BY*
Knox & Knox United States Patent Office Plant Pat. 1,868
Patented Sept. 22, 1959

1,868

MACADAMIA TREE

Ernest S. Burdick, Encinitas, Calif., assignor of one-half to Rodney B. Taylor, Encinitas, Calif.

Application November 7, 1957, Serial No. 695,184

1 Claim. (Cl. 47—62)

My new discovery relates to improvements in Macadamia trees, sometimes referred to as Macadamia nut trees.

My new tree is a seedling grown from a nut of uncertain origin planted by me in 1949 in a cultivated area, my own orchard, approximately one mile from the ocean at Encinitas in southern California.

The accompanying drawings illustrate the plant. The first view is an enlarged view of a single leaf and a group view of a nut with the shell cracked open in two parts and the kernel represented therebetween. The second view is a perspective view of a small branch with a number of leaves and a cluster of nuts thereon.

This new tree is a new and distinct variety of Macadamia, a member of the family Proteaceae and evidently a variety of the species *Macadamia tetraphylla*. The most outstanding distinguishing characteristic of my new Macadamia tree is the exceptionally large nuts which average forty to the pound. The nut is also characterized by its pebbly surface and by having an exceptionally thin shell, averaging one-sixteenth of an inch thick, and the kernel almost completely fills this shell. Frequently four racemes arise from a single node and produce a ball of nuts measuring approximately six inches thick. The average number of nuts per raceme is 25. When three or four racemes arise at a single node some of the nuts are crowded off before maturity, thus decreasing the size of the resultant, grape-like cluster. However, more nodes produce one, two or three racemes than four. The average weight of the kernel is 3.88 grams and the kernel represents 34.3 percent of the total weight of the nut.

The tree blossoms in early spring, producing pendulous racemes, slightly longer than the average for the species *M. tetraphylla*, the racemes being first green, then cream colored, darkening to brown. And the tree is characterized by consistent annual nut bearing and the nuts are self-hulling, with the nuts being shed onto the ground in October in the locale in which the tree is growing in southern California.

The bark of the tree is at least as smooth as any other known variety of Macadamia and has a brownish tinge with driftwood gray mottles.

Certain other Macadamia varieties have slightly spiney leaves which are sessile as is true in the instant case, but my tree is characterized by exceptionally long leaves. The length of the leaves varies from seven inches to twelve inches with an average length of approximately ten inches. Approximately ninety-five percent of the nodes have four leaves rising therefrom.

The tree has an irregular branching habit and is less bushy than other known varieties of Macadamia, with a tendency to grow slimmer and taller.

The tree has been asexually reproduced by grafting in the orchard at my home in Encinitas, California and the characteristics of the progeny are the same as of the parent tree.

Having thus disclosed my discovery, I claim:

A new and distinct variety of Macadamia tree, substantially as herein shown and described, characterized particularly as to novelty by the exceptionally large nut averaging forty to the pound, by the thin shell of the nut, by the self-hulling characteristic of the nut, by consistent annual nut bearing with the nuts being shed onto the ground in October (in southern California), by very smooth bark on both trunk and branches and brownish with driftwood gray mottles, by spiney leaves which are sessile and exceptionally long with an average length of ten inches.

No references cited.